United States Patent
Termer et al.

(10) Patent No.: US 11,820,900 B2
(45) Date of Patent: Nov. 21, 2023

(54) INTERFERENCE PIGMENTS

(71) Applicant: Merck Patent GmbH, Darmstadt (DE)

(72) Inventors: Michael Termer, Hofheim (DE); Jutta Zur Lage, Darmstadt (DE); Anett Moschner, Darmstadt (DE); Lilia Heider, Gernsheim (DE)

(73) Assignee: Merck Patent GmbH, Darmstadt (DE)

( * ) Notice: Subject to any disclaimer, the term of this patent is extended or adjusted under 35 U.S.C. 154(b) by 149 days.

(21) Appl. No.: 16/494,340

(22) PCT Filed: Mar. 14, 2018

(86) PCT No.: PCT/EP2018/056317
§ 371 (c)(1),
(2) Date: Sep. 16, 2019

(87) PCT Pub. No.: WO2018/167109
PCT Pub. Date: Sep. 20, 2018

(65) Prior Publication Data
US 2021/0115260 A1 Apr. 22, 2021

(30) Foreign Application Priority Data
Mar. 17, 2017 (EP) .................... 17161709

(51) Int. Cl.
| | | |
|---|---|---|
| *C09C 1/00* | (2006.01) | |
| *A61K 8/02* | (2006.01) | |
| *A61K 8/06* | (2006.01) | |
| *A61K 8/19* | (2006.01) | |
| *A61K 8/25* | (2006.01) | |
| *A61K 8/26* | (2006.01) | |
| *A61K 8/29* | (2006.01) | |
| *A61Q 1/02* | (2006.01) | |
| *A61Q 17/04* | (2006.01) | |

(52) U.S. Cl.
CPC .......... *C09C 1/0015* (2013.01); *A61K 8/0266* (2013.01); *A61K 8/062* (2013.01); *A61K 8/064* (2013.01); *A61K 8/19* (2013.01); *A61K 8/25* (2013.01); *A61K 8/26* (2013.01); *A61K 8/29* (2013.01); *A61Q 1/02* (2013.01); *A61Q 17/04* (2013.01); *A61K 2800/412* (2013.01); *A61K 2800/436* (2013.01); *A61K 2800/621* (2013.01); *A61K 2800/651* (2013.01); *C01P 2004/20* (2013.01); *C01P 2004/61* (2013.01); *C09C 2200/102* (2013.01); *C09C 2200/401* (2013.01); *C09C 2220/106* (2013.01)

(58) Field of Classification Search
CPC ............... C09C 1/0015; A61K 8/0266
See application file for complete search history.

(56) References Cited

U.S. PATENT DOCUMENTS

| | | |
|---|---|---|
| 8,936,799 B2 | 1/2015 | Schmid et al. |
| 9,815,970 B2 | 11/2017 | Jones et al. |
| 10,597,544 B2 | 3/2020 | Mathias et al. |
| 10,799,432 B2 | 10/2020 | Grüner et al. |
| 2004/0052743 A1 | 3/2004 | Schmidt et al. |
| 2010/0322981 A1 | 12/2010 | Bujard et al. |
| 2011/0226161 A1 | 9/2011 | Schumacher et al. |
| 2012/0091702 A1* | 4/2012 | Shimizu ............... C09C 1/0015 283/75 |
| 2012/0282311 A1 | 11/2012 | Schmid et al. |
| 2013/0164356 A1 | 6/2013 | Pfaff et al. |
| 2013/0216597 A1 | 8/2013 | Mathias et al. |
| 2015/0344677 A1 | 12/2015 | Jones et al. |
| 2016/0068683 A1 | 3/2016 | Pfaff et al. |
| 2020/0339820 A1 | 10/2020 | Pfaff et al. |

FOREIGN PATENT DOCUMENTS

| | | |
|---|---|---|
| EP | 2217665 B1 | 6/2011 |
| EP | 2607432 A1 | 6/2013 |
| EP | 2493987 B1 | 7/2014 |
| JP | 2004059921 A | 2/2004 |
| JP | 2013502468 A | 1/2013 |
| JP | 2013544919 A | 12/2013 |
| KR | 20100108518 A | 10/2010 |
| KR | 20130072158 A | 7/2013 |
| KR | 20130132826 A | 12/2013 |
| WO | 2016097417 A1 | 6/2016 |
| WO | 2016097418 A1 | 6/2016 |

OTHER PUBLICATIONS

International Search Report dated May 9, 2018 issued in corresponding PCT/EP2018/056317 application (3 pages).
English translation of Notice of Reasons for Refusal in corresponding JP 2019551371 dated Jan. 11, 2022 (pp. 1-3).
Office Action in corresponding Korean Patent Appln. No. 2019-7030376 dated Oct. 19, 2022 (pp. 1-11) and english translation thereof (pp. 1-11).

* cited by examiner

*Primary Examiner* — Gina C Justice
(74) *Attorney, Agent, or Firm* — MILLEN, WHITE, ZELANO & BRANIGAN, PC; Ryan Pool

(57) ABSTRACT

The present invention relates to interference pigments based on platelet-shaped substrates which are coated with at least four high refractive layers and to the use thereof, inter alia in paints, coatings, printings inks, plastics and in particular in cosmetic formulations. The interference pigments show a moderate chroma and can be used as effect pigments, as filler pigments and as protection agent against near infrared radiation, VIS and high energy light.

14 Claims, 3 Drawing Sheets

Fig. 1a: Transmission of HEV light through oil-in-water formulation
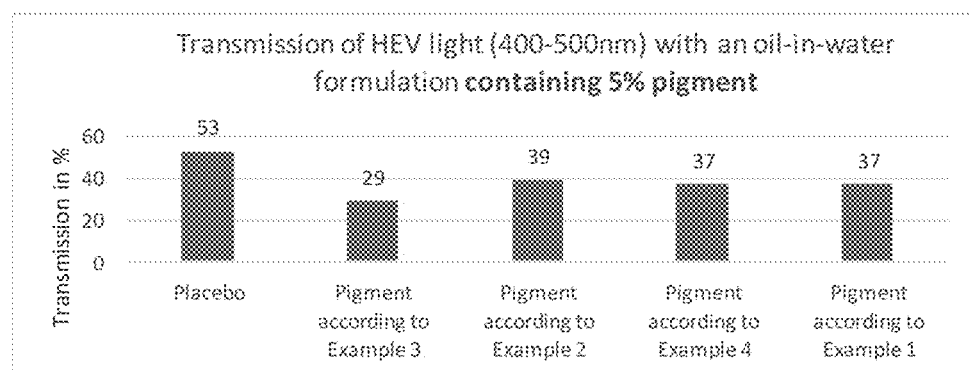
Fig. 1b: Transmission of HEV light through oil-in-water formulation
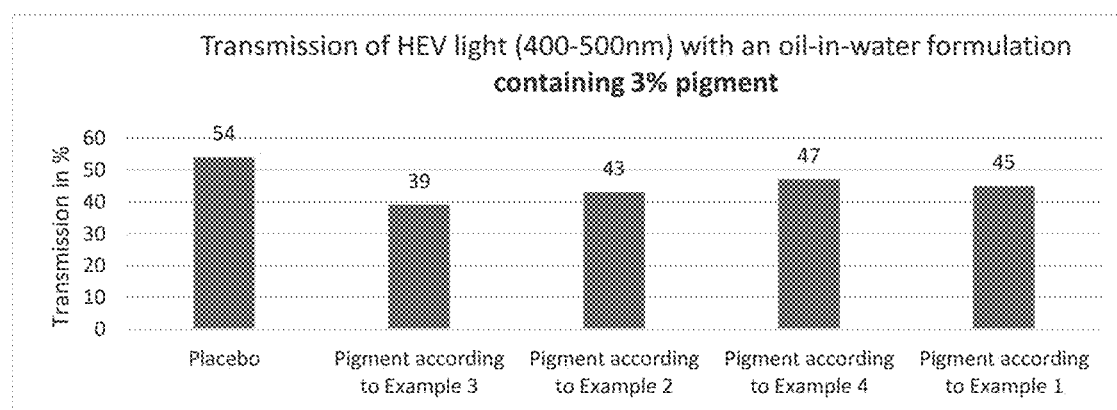

Fig. 2a: Transmission of VIS light through oil-in-water formulation
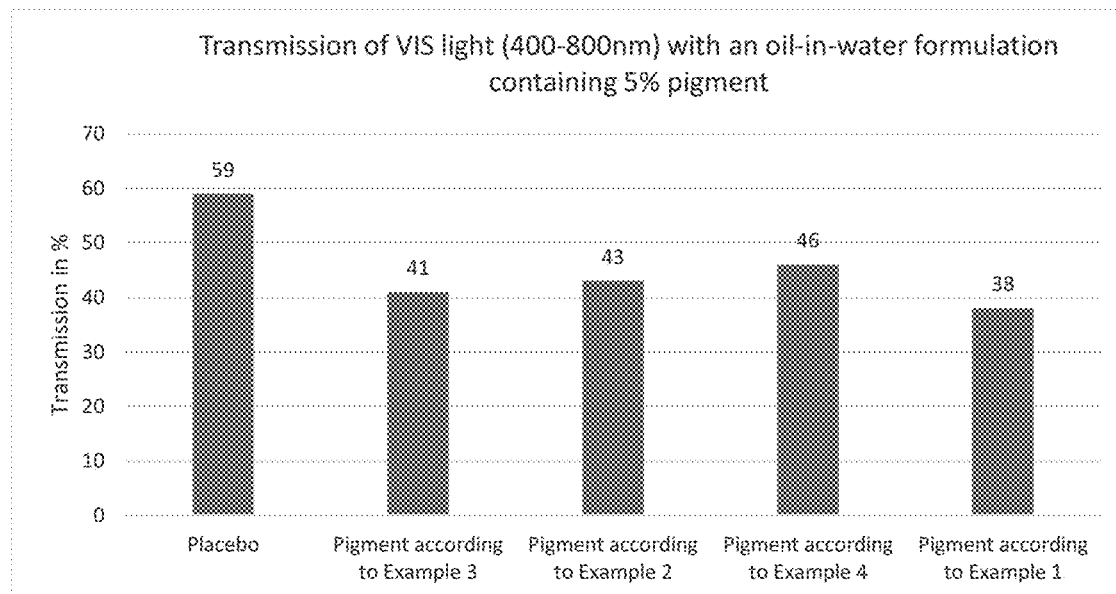
Fig. 2b: Transmission of VIS light through oil-in-water formulation
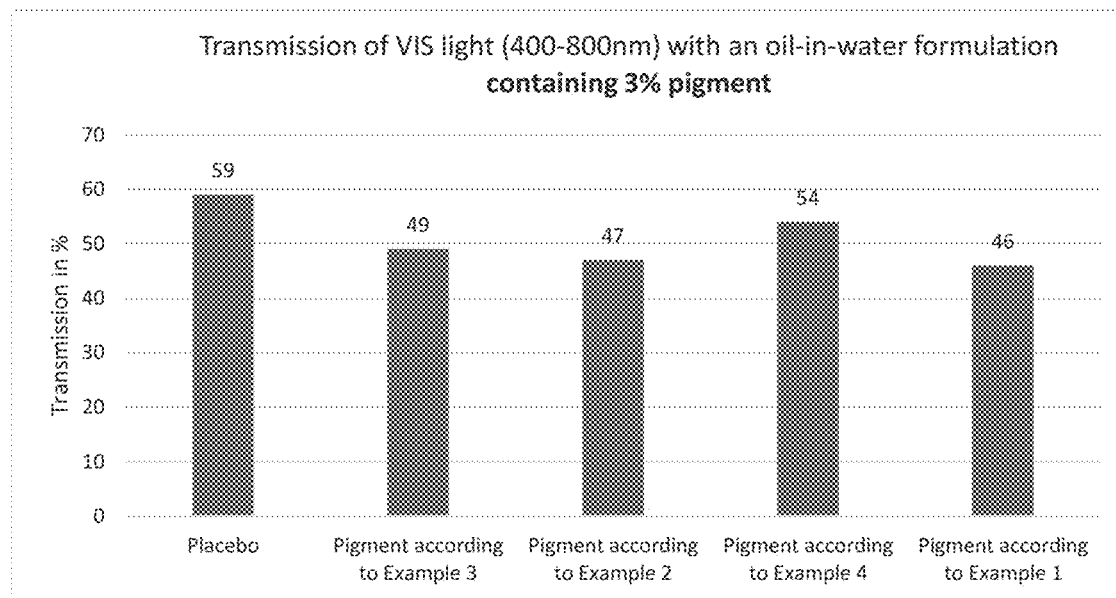

Fig. 3a: Transmission of IR-A light through oil-in-water formulation
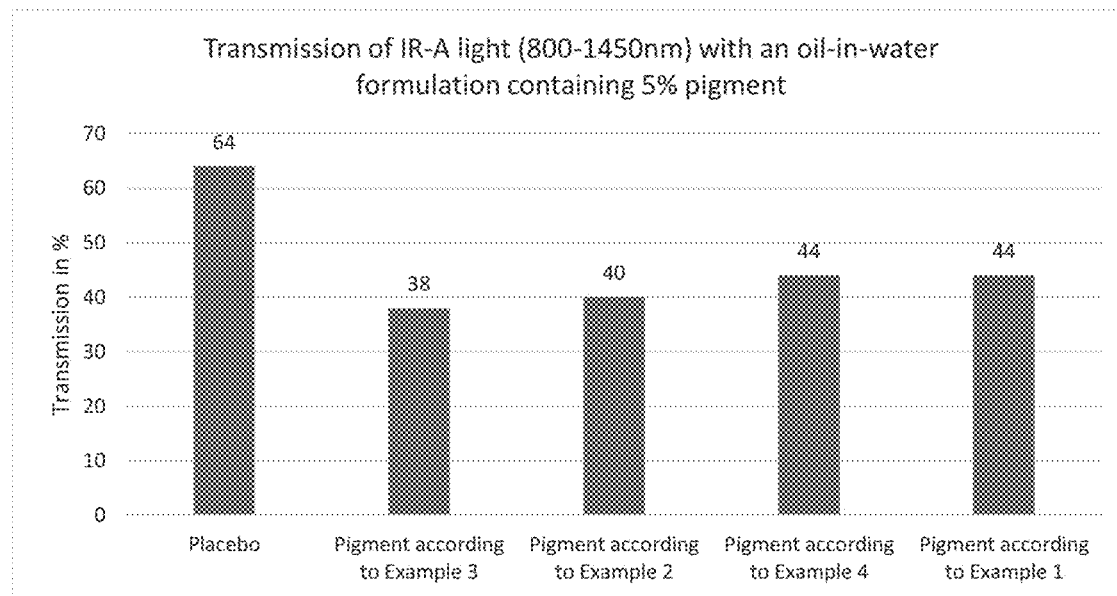
Fig. 3b: Transmission of IR-A light through oil-in-water formulation
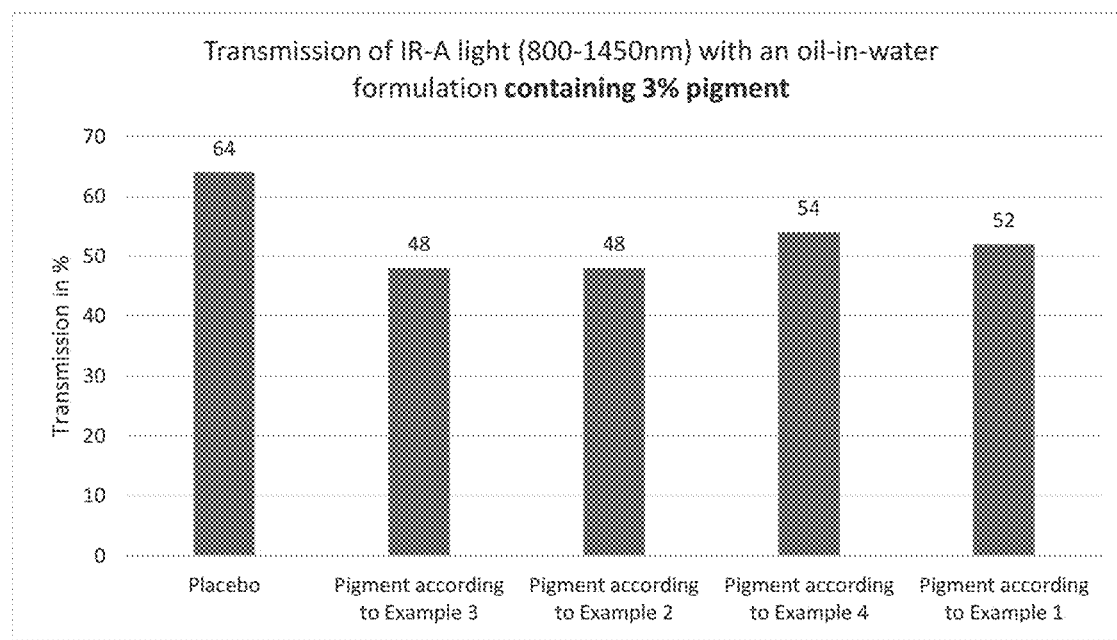

INTERFERENCE PIGMENTS

The present invention relates to interference pigments based on platelet-shaped substrates which are coated with at least four high refractive layers and to the use thereof, inter alia in paints, coatings, printings inks, plastics and in particular in cosmetic formulations. The interference pigments show a moderate chroma and can be used as effect pigments, as filler pigments and as protection agent against near infrared radiation, VIS and high energy light.

The solar spectrum is composed of various wavelength radiations having specific as well as overlapping and synergistic effects on skin. UVB is responsible for most sunburn, although short wavelength UVA may also trigger erythema to a lesser extent. Both UVB and UVA alter the immune response either alone or together, but given that UVA is 20 times more abundant in sunlight, the latter is generally considered the main culprit in solar-induced immune suppression.

Visible light mainly affects skin through the generation of oxidative damage, whereas IR induces heat damage and alters mitochondrial integrity in skin cells, resulting in ROS (radical oxygen species) generation.

Nearly 50% of free radicals formed by solar radiation are deriving from visible and IR light. IR-A (800 to 1450 nm) and high energy visible (HEV) light (400-500 nm) also called "blue light" leads to a significant degradation of cutaneous carotenoid antioxidants.

All solar wavelengths contribute altogether to photoaging of the skin due to ROS/RNS (radical oxygen species/radical nitrogen species) generation. It is therefore necessary to develop skin care or sun care products not only with an UVB/UVA protection but also in addition with HEV and IR-A protection for maintenance of skin health.

In cosmetics, it is known that the addition of an inorganic pigment and in particular of a titanium dioxide ($TiO_2$) pigment enables the light-protection properties of sunscreens comprising UV filters to be improved. But $TiO_2$ acts as a white pigment and a filler pigment, i.e. has an influence on the skin feeling and on the texture of the application, and thus has an influence on the optical properties, such as color and gloss, of the final cosmetic products, in particular for the decorative cosmetics. It reduces the color intensity and the gloss effect of cosmetic formulations containing effect pigments.

The object of the present invention is to provide an effect pigment with lower gloss but pure interference colours which shows the properties of a filler with regard to the skin-feeling and which is able to protect the skin against VIS (400-800 nm), HEV (400-500 nm) and IR-A (800-1450 nm) radiance.

Surprisingly, it has now been found that interference pigments based on platelet-shaped substrates with a defined particle size and coated with four high refractive layers with a defined layer structure show very pure colors, lower luster compared to commercially available interference pigments, good skin feeling and at the same time protect the skin against VIS, HEV and IR-A.

Thus, the present invention therefore relates to interference pigments based on platelet shaped substrates with a particle diameter in the range 0.1-100 μm which are coated on the surface with four layers (A) to (D),
whereas
(A) is a highly refractive index layer which essentially consist of $SnO_2$
(B) is a highly refractive index layer which essentially consist of $TiO_2$
(C) is a highly refractive index layer which essentially consist of $SnO_2$
(D) is a highly refractive index layer which essentially consist of $TiO_2$
and optionally
(E) an outer protective layer.

The interference pigments according to the present invention exhibit
high chroma
pure interference colours
excellent skin-feeling
highly suitable skin color modification
natural freshness and luminosity to any skin type
skin protection against IR-A, VIS and HEV radiation
ready dispersibility in aqueous and oily phases
easy and homogeneous distribution on the skin
simple and homogeneous incorporation into any kind of formulations.

The invention furthermore relates to a process for the preparation of the interference pigments according to the invention.

The present invention likewise relates to the use of the interference pigments according to the invention in paints, automotive paints, industrial coatings, automotive refinish paints, powder coatings, printing inks, plastics, button pastes, ceramic materials, glasses, for coating seed, as additive for the laser welding of plastics, as dopant in the laser marking or in the laser welding of plastics and papers, as additive for colouring in the foods and pharmaceuticals sector and in cosmetic formulations. The pigments according to the invention are furthermore also suitable for the preparation of pigment preparations and for the preparation of dry preparations, such as, for example, granules, chips, pellets, briquettes, etc. The dry preparations are suitable, in particular, for printing inks and for cosmetic formulations.

An essential feature for the interference pigments according to the invention is the particle size of the base substrate in combination with the coating layer sequence on the surface of the substrate.

Suitable base substrates for the pigments according to the invention are colourless or selectively or non-selectively absorbent flake-form substrates. Suitable substrates are, in particular, phyllosilicates, such as natural or synthetic mica, talc, kaolin, flake-form iron or aluminium oxides, perlite flakes, glass flakes, $SiO_2$ flakes, $TiO_2$ flakes, graphite flakes, synthetic support-free flakes, titanium nitride, titanium silicide, liquid crystal polymers (LCPs), holographic pigments, BiOCl and flake-form mixed oxides, or mixtures thereof. Particularly preferred substrates are glass flakes, $SiO_2$ flakes, natural or synthetic mica flakes and $Al_2O_3$ flakes. Natural and synthetic mica flakes are especially preferred.

The size of the base substrates is not crucial per se and can be matched to the particular application. Preferably the flake-form substrates have a thickness of 100-1500 nm, in particular 100-500 nm. The size in the two other dimensions is 0.1-100 μm, preferably 0.1-60 μm, in particular 0.1 25 μm.

The base substrates of the interference pigments preferably have a thickness of <300 nm with an equivalence diameter distribution ($D_{90}$) according to which 90% of the particles are in the range from 100-300 μm.

Suitable glasses for the synthetically prepared glass flakes are all glasses known to the person skilled in the art, for example silicate glasses, such as soda-lime glass, borosilicate glass, aluminosilicate glass, lead crystal glass, E, A, C or ECR glass, Duran glass, window glass, laboratory glass, etc. Glasses of this type are produced from sand, lime, clay, boron compounds, potash, soda, etc. and allowed to solidify in a shaped state. Suitable glass flakes preferably consist of C, E, ECR or borosilicate glass. It is of course also possible to employ mixtures of different glass flakes which only differ in the glass composition. Particular preference is given to substrate flakes comprising calcium aluminium borosilicate or ECR glass.

The glass flakes can be specifically coloured during production by addition of inorganic colorants. Suitable colorants are those which do not decompose at the melting point of the glass. The colorant is generally added to the glass melt in amounts of 0.1-50% by weight, in particular 0.2-25% by weight and very particularly preferably 0.5-10% by weight.

Suitable colorants are, in particular, the cations or complex anions of the elements Cu, Cr, Mn, Fe and Co and/or combinations thereof. Intense blue, green, yellow, orange or red colours can be obtained by addition of the ions. Suitable colorants are furthermore $TiO_2$ or elemental noble metals.

The refractive index of suitable glass flakes is preferably 1.45-1.80, in particular 1.50-1.70.

It is frequently advisable to provide the surface of the glass flakes with a $SiO_2$ layer before the covering with layers (A)-(D) or (A)-(E). However, the covering with the $SiO_2$ layer (layer (A0)) means that the chemical composition of the glass flakes is of secondary importance for the further coatings and the resultant applicational properties of the pigments. The $SiO_2$ covering protects the glass surface against chemical modification, such as swelling, leaching-out of glass constituents or dissolution in the aggressive acidic covering solutions.

Particular preference is given to glass flakes having an average thickness of <2 μm, preferably of ≤1 μm. Thicker flakes generally cannot be employed in common printing processes and in demanding paint finishes. The glass flakes preferably have average thicknesses of <1 μm, in particular <0.9 μm. Particular preference is given to glass flakes having thicknesses of 50-3000 nm. The diameter of the glass flakes is 0.1-100 μm, preferably 0.1-60 μm, particularly preferably 0.1-25 μm. Glass flakes having these dimensions are commercially available.

Particular preference is given to interference pigments based on natural or synthetic mica flakes.

The interference pigments according to the present invention preferably have the following particle size distributions:

The $D_{10}$ values are preferably in the range from 1-4 μm, very particularly preferably in the range from 1.5-3.5 μm.

The $D_{50}$ values are preferably in the range from 4-8 μm, very particularly preferably in the range from 4.5-7.5 μm.

The $D_{90}$ values are preferably in the range from 8-15 μm, very particularly preferably in the range from 8.5-14.5 μm.

The interference pigments based on mica flakes preferably have the following particle size distributions:
$D_{10}$: 3-5.5, preferably 3.5-5,
$D_{50}$: 6-9, preferably 6.5-8.5,
$D_{90}$: 11-15.5, preferably 11.5-15, The thickness of the mica flakes is preferably 100-450 nm. The form factor (diameter/thickness ratio) of the mica flakes is preferably in the range of 30-60.

The characterisation of the particle size distribution is carried out in this patent application by means of laser diffraction. In the present application, the particle size distribution is determined using the Malvern Mastersizer 2000 instrument.

The thickness of the individual layers having a high refractive index, i.e. $TiO_2$ layer and $SnO_2$ layer on the base substrate is essential for the optical properties of the pigment. For a pigment having pure interference colours and moderate chroma, the thickness of the individual layers must be adjusted accurately to one another. It has been found that the sum of all layers on the substrate should not exceed a thickness of 1000 nm, preferably ≤800 nm.

The interference pigments according to the invention comprise four high-refractive-index layers (A)-(D) which essentially consist of $SnO_2$ or $TiO_2$.

Essentially means that the layers consist at least of 90%, preferably ≥95% $SnO_2$ or $TiO_2$ based on each layer and most preferably consist of 100% of $SnO_2$ or $TiO_2$.

The layers (A) to (D) can be doped with colorants such as carbon black, alkali metals, earth alkaline metals.

In a preferred embodiment the interference pigment contains one or more layers which are doped with at least one alkali metal and/or at least one alkaline earth metal. Preferably the alkaline earth metal is selected from Mg and/or Ca. The amount of dopant is preferably in the range of 0.01-10 wt. %, in particular 0.05-5 wt. % based on the pigment.

The thickness of coating layer (A) is preferably 1-5 nm, in particular 2-4 nm and very particularly preferably 2-3 nm.

The thickness of coating layer (B) is preferably 100-350 nm, in particular 100-300 nm and very particularly preferably 100-250 nm.

The thickness of coating layer (C) is preferably 1-5 nm, in particular 2-4 nm and very particularly preferably 2-3 nm.

The thickness of coating layer (D) is preferably 100-350 nm, in particular 100-300 nm and very particularly preferably 100-250 nm.

The thickness of the $SiO_2$ layers (A) and (C) can be identical or different. The $TiO_2$ layers (B) and (D) can have the same or different thicknesses depending on the requested interference color.

The thickness of layers (A) to (D) depend on the desired interference colour of the interference pigment according to the present invention.

Particularly preferred interference pigments have the following layer sequences on the platelet-shaped substrate:

Synthetic mica+$SnO_2$+$TiO_2$+$SnO_2$+$TiO_2$

Natural mica+$SnO_2$+$TiO_2$+$SnO_2$+$TiO_2$ $Al_2O_3$ flakes+$SnO_2$+$TiO_2$+$SnO_2$+$TiO_2$ $SiO_2$ flakes+$SnO_2$+$TiO_2$+$SnO_2$+$TiO_2$ Glass flakes+$SiO_2$+$SnO_2$+$TiO_2$+$SnO_2$+$TiO_2$ Glass flakes+$SnO_2$+$TiO_2$+$SnO_2$+$TiO_2$.

High-refractive-index coatings in this application are taken to mean layers having a refractive index of ≥1.8, low-refractive-index layers are taken to mean those where n<1.8.

Layer or coating in this application is taken to mean the complete covering of the substrate and of the first layer and of the second layer, etc.

The interference pigments according to the invention can be prepared by means of a simple process.

In the case of wet coating, the interference pigments according to the invention are generally prepared by suspending the base substrates in water, optionally mixed with a water-glass solution, and then with one or more hydrolysable tin and titanium salts at a pH which is suitable for hydrolysis, which is selected so that the $SiO_2$, if present, preferably in the case of the covering of glass flakes, and the metal oxide(s) or metal oxide hydrate(s) are precipitated directly onto the flake, simultaneously or successively, without secondary precipitations occurring. The pH is usually kept constant by simultaneous metered addition of a base and/or acid. The pigments are subsequently separated off, washed and dried at 50-150° C. for 1-18 h and optionally calcined for 0.5-3 h, where the calcination temperature can be optimised with respect to the coating present in each case. In general, the calcination temperatures are in the range from 600-1100° C., preferably 700-1000° C. In the case of the use of glass flakes as substrate, the calcination temperature is preferably in the range from 500-800° C. Finally, the pigment is sieved. If desired, the pigments can be separated off, dried and optionally calcined after application of individual coatings and then re-suspended again for the precipitation of the further layers.

For the preparation of doped $TiO_2$ and/or $SnO_2$ layers an aqueous solution of at least one alkali metal compound and/or at least one alkaline earth metal compound is additionally added simultaneously with the hydrolysable tin and titanium salts.

Furthermore, the coating can also be carried out in a fluidised-bed reactor by gas-phase coating, it being possible to use correspondingly, for example, the methods proposed in EP 0 045 851 and EP 0 106 235 for the preparation of pearlescent pigments.

The color of the interference pigments can be varied in very broad limits through the different choice of the covering amounts or the layer thicknesses resulting therefrom. Fine tuning for a certain hue can be achieved beyond the pure choice of amount by approaching the desired colour under visual or measurement-technology control.

The resultant interference pigments having the four highly refractive layers are distinguished by pure colours, moderate chroma and a high skin feeling and show light protection against near infrared radiation (800-1400 nm) and high energy light (400-500 nm).

In order to increase the light, water and weather stability and/or to improve the wettability and/or compatibility, it is frequently advisable, depending on the area of application, to subject the finished interference pigment to inorganic or organic post-coating or post-treatment. Suitable post-coatings or post-treatments are the processes described, for example, in German patent 22 15 191, DE-A 31 51 354, DE-A 32 35 017 or DE-A 33 34 598. This post-coating further increases the chemical stability or simplifies handling of the pigment, in particular incorporation into various media. In order to improve the wettability, dispersibility and/or compatibility with the application media, functional coatings comprising $Al_2O_3$ or $ZrO_2$ or mixtures or mixed phases thereof may be applied to the pigment surface. Furthermore, organic or combined organic/inorganic post-coatings are possible, for example with silanes, as described, for example, in DE 10348174, EP 0090259, EP 0 342 533, EP 0 632 109, EP 0 888 410, EP 0 634 459, EP 1 203795, WO 94/01498, WO 96/32446, WO 99/57204, WO 2004/092284, U.S. Pat. Nos. 5,759,255, 5,571,851, WO 01/92425, JP-A-63-130673, JP-A-1-292067, JP-A-2001-106937, JP-A-2001-164150, JP-A-2001-220522, JP-A-08-283604, JP-A-03-100068, JP-A-08-283604 or in J. J. Ponjeé, Philips Technical Review, Vol. 44, No. 3, 81 ff. and P. H. Harding J. C. Berg, J. Adhesion Sci. Technol. Vol. 11 No. 4, pp. 471-493. The post-coating includes merely a proportion by weight of 0.1 to 5% by weight, preferably 0.5 to 3% by weight, based on the interference pigment. Layer (E) preferably has thicknesses of 0.1-100 nm, in particular 0.1-50 nm and very particularly preferably 0.1-30 nm.

In a preferred embodiment, layer (E) consists of a $SiO_2$ layer. This layer may be either calcined or non-calcined. It is preferably a calcined $SiO_2$ layer.

The concentration of the pigment according to the invention in the application system to be pigmented is generally between 0.1 and 100% by weight, preferably between 0.1 and 70% by weight and in particular between 0.5 and 10% by weight, based on the total solids content of the system. It is generally dependent on the specific application.

It goes without saying that, for the various applications, the interference pigments according to the invention may also advantageously be used as a mixture with one or more colorants, for example effect pigments selected from the group of the pearlescent pigments, interference pigments, gonio-chromatic pigments, coated or uncoated BiOCl flakes, multilayered pigments, metal pigments, lustre pigments, and/or organic dyes, and/or organic coloured pigments and other pigments, such as, for example, transparent and opaque white, coloured and black pigments, and also with platelet-shaped iron oxides, holographic pigments, LCPs (liquid crystal polymers) and conventional transparent, coloured and black lustre pigments based on metal oxide-coated mica flakes and $SiO_2$ flakes, etc. Novel hues and functions can be uncovered as a result of combining these pigments etc. with the interference pigments according to the present invention.

The interference pigments according to the invention can be mixed with a colorant in any ratio. The interference pigment to colorant weight ratio can be 1:99 to 99:1, depending on the colour intensity and the application.

Suitable colorants are, in particular, pearlescent pigments, in particular based on natural or synthetic mica, $SiO_2$ flakes, $Fe_2O_3$ flakes, glass flakes or $Al_2O_3$ flakes, which are covered with one or more metal-oxide layers, metal-effect pigments (Al flakes, bronzes), optically variable pigments (OVPs), liquid-crystal polymer pigments (LCPs) or holographic pigments.

Besides the interference pigments as admixture, predominantly non-lustrous, conventional colorants are also particularly suitable, such as, for example, $TiO_2$, coloured $SiO_2$, $CaSO_4$, iron oxides, chromium oxides, carbon black, organic coloured pigments, such as, for example, anthraquinone pigments, quinacridone pigments, diketopyrrolopyrrole pigments, phthalocyanine pigments, azo pigments, isoindoline pigments. Also suitable are, for example, coloured glass fibres, α-FeOOH, organic coloured pigments, such as, for example, azo pigments, β-phthalocyanine CI Blue 15.3, Cromophtal Yellow 8GN (Ciba-Geigy), Irgalith Blue PD56 (BASF), azomethine/copper complex CI Yellow 129, Irgazine Yellow 5GT (BASF) or a mixture of the said colorants. The colorants here may be both of natural or also synthetic origin.

Examples of particular preferred organic pigments include red nos. 2, 3, 102, 104, 105, 106, 201, 202, 203, 204, 205, 206, 207, 208, 213, 214, 215, 218, 219, 220, 221, 223, 225, 226, 227, 228, 230-1, 230-2, 231, 232, 405; yellow nos. 4, 5, 201, 202-1, 202-2, 203, 204, 205, 401, 402, 403, 404, 405, 406, 407; green nos. 3, 201, 202, 204, 205, 401, 402; blue nos. 1, 2, 201, 202, 203, 204, 205, 403, 404; orange nos. 201, 203, 204, 205, 206, 207, 401, 402, 403; brown no. 201; violet nos. 201, 401; black no. 401. Examples of natural colors include salol yellow, carmine, β-carotin, hibiscus color, capsaicin, carminic acid, laccaic acid, gurcumin, riboflavin, shikonin, etc. Also advantageous are oil-soluble natural dyes, such as, for example, paprika extract, β-carotene or cochineal, in particular β-carotene.

The interference pigments according to the invention can of course also be mixed or employed with fillers in any weight ratio. Fillers which may be mentioned are, for example, synthetic organic polymers, polymethyl methacrylate, methyl methacrylate crosspolymer, natural and synthetic mica, nylon powder, pure or filled melamine resins, talc, $SiO_2$, glass powder, glass beads, kaolin, oxides or hydroxides of aluminium, magnesium, calcium, zinc, BiOCl, barium sulfate, calcium sulfate, calcium carbonate, magnesium carbonate, basic alkaline-earth metal carbonates, such as, for example, calcium carbonate or magnesium carbonate, carbon, and physical or chemical combinations of these substances. There are no restrictions regarding the particle shape of the fillers. In accordance with requirements, it can be, for example, irregular, flake-form, spherical or needle-shaped.

Finely divided, in particular nanoscale dielectrics may likewise be admixed with the interference pigments, in particular in cosmetic formulations, in order to improve the skin feeling. Examples of additions of this type are $Al_2O_3$, $SiO_2$, ZnO or $TiO_2$, which are usually added to the formulation in amounts of 0.01-15% by weight.

The interference pigments according to the invention are compatible with a multiplicity of colour systems, preferably from the area of paints, surface coatings and printing inks. For the preparation of printing inks for, for example, gravure printing, flexographic printing, offset printing, offset overprint varnishing, a multiplicity of binders, in particular water-soluble grades, is suitable, as marketed, for example, by BASF, Marabu, Pröll, Sericol, Hartmann, Gebr. Schmidt, Sicpa, Aarberg, Siegberg, GSB-Wahl, Follmann, Ruco or Coates Screen INKS GmbH. The printing inks can be water-based or solvent-based. Furthermore, the interference pigments according to the invention are also suitable for the laser marking of paper and plastics, and for applications in the agricultural sector, for example for greenhouse sheeting, and, for example, for colouring tarpaulins.

In the case of pigmenting of binder systems, for example for surface coatings and printing inks for gravure printing, offset printing or screen printing, or as precursors for printing inks, the use of the interference pigments according to the invention in the form of highly pigmented pastes, granules, pellets, etc., has proven particularly suitable. The interference pigment according to the invention is generally incorporated into the printing ink in amounts of 2-35% by weight, preferably 5-25% by weight and in particular 8-20% by weight. Offset printing inks can comprise the pigments with a proportion of up to 40% by weight or more. The precursors of printing inks, for example in the form of granules, as pellets, briquettes, etc., comprise up to 98% by weight of the pigment according to the invention besides the binder and the additives. Printing inks which comprise the interference pigment according to the invention generally exhibit purer hues than printing inks comprising conventional effect pigments.

The interference pigments according to the invention are furthermore suitable for the preparation of flowable pigment compositions and dry preparations, in particular for printing inks, comprising one or more pigments according to the invention, binders and optionally one or more additives.

In plastics comprising the interference pigment according to the invention, preferably in amounts of 0.01 to 50% by weight, in particular 0.1 to 7% by weight, particularly pronounced colour effects can be achieved.

In the surface coatings area, in particular in automobile paints, the interference pigment is employed in amounts of 0.1-20% by weight, preferably 1 to 10% by weight, including for 3-coat systems. Decorative painting of automobiles is typically carried out in 2 coats: firstly, a decorative coat, i.e. comprising the colour-determining pigments, is sprayed onto the primer. This is followed by painting with a clear coat, which enhances the colour and increases the gloss. In addition, the clear coat makes a crucial contribution to the weather stability and durability of the finish.

Furthermore, the pigment according to the invention can be employed for the finishing of foods, for example mass colouring and/or coatings of boiled sweets, wine gums, such as, for example, jelly babies, pralines, liquorice, confectionery, sticks of rock, blancmange, fizzy drinks, sodas, etc., or as a coating, for example, in dragees and tablets in the pharmaceutical area.

The interference pigment according to the invention can also advantageously be employed in decorative and care cosmetics. The use concentration extends from 0.01% by weight in shampoo to 100% by weight in the case of loose powders. In the case of a mixture of the pigments according to the invention with fillers, preferably with spherical fillers, such as, for example, $SiO_2$, the concentration in the cosmetic formulation can be 0.01-70% by weight. The cosmetic products, such as, for example, nail varnishes, compact powders, shampoos, loose powders and gels, are distinguished by particularly interesting colour effects and high gloss.

No limits are set for the concentrations of the interference pigments according to the invention in the cosmetic formulation. They can be—depending on the application—between 0.001 (rinse-off products, for example shower gels) and 100% (for example lustre-effect articles for particular applications).

Owing to the good skin feeling and the very good skin adhesion, the interference pigments according to the invention are suitable both for personal care applications, such as, for example, body lotions, emulsions, shampoos, soaps, etc., and also, in particular, for decorative cosmetics.

The interference pigments according to the invention can of course also be combined in the formulations with any type of raw materials and assistants and active compounds. These include, inter alia, water, alcohols, polyols, polar and nonpolar oils, fats, waxes, film formers, polymers, copolymers, surfactants, free-radical scavengers, antioxidants, such as, for example, vitamin C or vitamin E, stabilisers, odour enhancers, silicone oils, emulsifiers, fragrances, solvents, such as, for example, ethanol, ethyl acetate or butyl acetate, preservatives and assistants which generally determine the applicational properties, such as, for example, thickeners and rheological additives, such as, for example, bentonites, hectorites, silicon dioxides, Ca silicates, gelatine, high-molecular-weight carbohydrates and/or surface-active assistants, etc.

The interference pigments can be combined with suitable active compounds are, for example, insect repellents, inorganic UV filters, such as, for example, $TiO_2$, UV A/BC protection filters (for example OMC, B3, MBC), including in encapsulated form, anti-ageing active compounds, vitamins and derivatives thereof (for example vitamin A, C, E, etc.), self-tanning agents (for example DHA, erythrulose, inter alia) and further cosmetic active compounds, such as, for example, bisabolol, LPO, VTA, ectoin, emblica, allantoin, bioflavonoids and derivatives thereof.

Organic UV filters are generally incorporated into cosmetic formulations in an amount of 0.5 to 10% by weight, preferably 1 to 8% by weight, and inorganic filters in an amount of 0.1 to 30% by weight.

The interference pigments according to the invention can be used, for example, in lipsticks, lip gloss, rouge, eyeliner, eye shadow, (volume) mascara, nail varnishes, day creams, night creams, body lotions, cleansing milk, body powders, hair gels, hair masks, hair rinses, hair shampoos, shower gels, shower oils, bath oils, sunscreen, pre-sun and after-sun preparations, tanning lotions, tanning sprays, make-ups, lotions, soaps, bath salts, toothpaste, face masks, compact powders, loose powders and gels, etc. Products of this type are produced in a manner as is known to the person skilled in the art in this area.

The formulations comprising the interference pigments according to the invention can belong to the lipophilic, hydrophilic or hydrophobic type. In the case of heterogeneous formulations having discrete aqueous and nonaqueous phases, the effect pigments according to the invention may in each case be present in only one of the two phases or alternatively distributed over both phases.

The pH values of the formulations can be between 1 and 14, preferably between 2 and 11 and particularly preferably between 5 and 8.

Further, examples of other components include fats and oils, waxes, surfactants, oxidation inhibitors, UV absorbers, vitamins, hormones, squalanes, liquid paraffins, palmitic acids, stearic acids, bees wax, myristyl myristate and other esters; acetone, toluene, butyl acetate, acetic ester and other solvents; antioxidants, antiseptic agents, polyhydric alcohols, perfumes, etc.

In a preferred embodiment, the cosmetic formulations containing the interference pigment according to the invention, comprise a cosmetically or dermatologically suitable vehicle and, depending on the desired property profile, optionally further suitable ingredients.

The cosmetic formulations containing the interference pigment according to the invention can be prepared by processes which are well known to the person skilled in the art, in particular by the processes which serve for the preparation of oil-in-water emulsions or water-in-oil emulsions.

The cosmetic formulations containing the interference pigment according to the invention relates to a process for the preparation of a composition which is characterised in that at least one interference pigment according to the present invention is mixed with a cosmetically or dermatologically suitable vehicle.

These formulations can be, in particular, in the form of simple or complex emulsions (O/W, W/O, O/W/O or W/O/W), such as creams, milks, gels or gel creams, powders and solid sticks, and they may, if desired, be formulated as aerosols and be in the form of foams or sprays. The formulations are preferably in the form of an O/W emulsion.

Examples which may be mentioned of application forms of the formulations are: solutions, suspensions, emulsions, PIT emulsions, pastes, ointments, gels, creams, lotions, powders, soaps, surfactant-containing cleansing preparations, oils. Examples of other application forms are sticks, shampoos and shower products. Any desired customary vehicles, assistants and, if desired, further active ingredients may be added to the composition.

Preferred assistants originate from the group of preservatives, antioxidants, stabilisers, solubilisers, vitamins, colorants, odour improvers.

Ointments, pastes, creams and gels may comprise the customary vehicles, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerin fatty acid esters, polyethylene glycols and fatty acid esters of sorbitan, or mixtures of these substances.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerin, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerin fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Cosmetic and dermatological compositions according to the invention may exist in various forms. Thus, they may be, for example, a solution, a water-free composition, an emulsion or microemulsion of the water-in-oil (W/O) type or of the oil-in-water (O/W) type, a multiple emulsion, for example of the water-in-oil-in-water (W/O/W) type, a gel, a solid stick, an ointment or an aerosol. It is also advantageous to administer ectoins in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Emulsions according to the invention are advantageous and comprise, for example, the said fats, oils, waxes and other fatty substances, as well as water and an emulsifier, as usually used for a composition of this type.

In a preferred embodiment the pigments according to the present invention are used in concentrations of 0.1 to 20 wt. %, in particular 0.1 to 10 wt. % and most preferably 0.1 to 5 wt. % based on the total composition in oil-in-water, water-in-oil emulsions, water-in-silicone or gels.

The interference pigments can be incorporated in the external phase, internal phase or the final emulsion/gel and in combination with one or more organic and/or inorganic UV filters.

Due to the fact that the interference pigment according to the present invention protects against HEV, VIS and IR-A radiation the pigment is highly suitable in a broad range of cosmetic applications, especially in care and decorative cosmetics. These are suitable for protection of the skin, lips, hair, scalp, hands, nails, eyebrows, eyelids, especially for protection of the areas described against photo- and/or oxidatively induced stress. In particular the interference pigments are highly suitable for sun care, foundations, BB (Blemish Balm), OTC (over the counter), whitening cosmetics or whitening serum for day use, UV and NIR protection.

The invention relates, in particular, to formulations which, besides the interference pigment according to the invention, comprise at least one constituent selected from the group of the absorbents, astringents, antimicrobial substances, antioxidants, antiperspirants, antifoaming agents, antidandruff active compounds, antistatics, binders, biological additives, bleaches, chelating agents, deodorisers, emollients, emulsifiers, emulsion stabilisers, dyes, humectants, film formers, fillers, fragrances, flavours, insect repellents, preservatives, anticorrosion agents, cosmetic oils, solvents, oxidants, vegetable constituents, buffer substances, reducing agents, surfactants, propellant gases, opacifiers, UV filters and UV absorbers, denaturing agents, viscosity regulators, perfume and vitamins.

The invention furthermore also relates to the use of the pigments in formulations, such as paints, surface coatings, industrial coatings, coil coating, automobile paints, automotive refinish paints, automobile paints, powder coatings, printing inks, security printing inks, plastics, ceramic materials, glasses, paper, in toners for electro photographic printing processes, in seed, in greenhouse sheeting and tarpaulins, as absorbers in the laser marking of paper and plastics, in cosmetic formulations, for the preparation of pigment pastes with water, organic and/or aqueous solvents, for the preparation of pigment compositions and dry preparations, such as, for example, granules, pellets, chips, briquettes, for the mass colouring of foods, for the colouring of coatings of food products and pharmaceutical products, for example as coating in the case of dragees and tablets.

The following examples explain the present invention in greater detail without restricting the scope of protection. In particular, the features, properties and advantages described in the examples of the compounds on which the relevant examples are based can also be applied to other substances and compounds which are not mentioned in detail, but fall within the scope of protection, unless stated otherwise elsewhere. In addition, the invention can be carried out throughout the range claimed and is not restricted to the examples mentioned here. Percentages given in this patent application are always weight %.

EXAMPLES

Example 1

175 g of fine-mica powder of 1 to 15 μm (average particle diameter: 6.5 μm) are suspended in 2.5 liters of deionized water. The suspension is heated to 75° C. while stirring. The pH is adjusted to 9.5 by adding sodium hydroxide. 335 ml of aqueous solution of $SnCl_4$ (53 g/l) containing HCl solution is added at the rate of 3.5 ml/min to the suspension in controlling the pH 1.8 by simultaneous addition of aqueous NaOH solution.

250 ml of aqueous solution of $TiCl_4$ (400 g/l) is added at the rate of 3.0 ml/min to the suspension in controlling the pH 1.8 by simultaneous addition of aqueous NaOH solution. Then 335 ml of aqueous solution of $SnCl_4$ (53 g/l) containing HCl solution is added at the rate of 3.5 ml/min to the suspension in controlling the pH 1.8 by simultaneous addition of aqueous NaOH solution. After adding the aqueous solution of $SnCl_4$ the aqueous solution of $TiCl_4$ (400 g/l) is added at the rate of 5.0 ml/min to the suspension in controlling the pH 1.8 by simultaneous addition of aqueous NaOH solution.

After reaching to end point of Gold.

The pH value of the suspension is controlled pH 9.0 by adding aqueous NaOH solution. The suspension containing mica coated with metal hydroxide is filtrated and washed by deionized water. The filter cake is dried at 110° C. and the dried product is calcinated at 750° C.

Example 2

122.5 g of fine-mica powder of 1 to 15 μm (average particle diameter: 6.5 μm) are suspended in 1.75 liters of deionized water. The suspension is heated to 75° C. while stirring. The pH is adjusted to 9.5 by adding sodium hydroxide. 265 ml of aqueous solution of $SnCl_4$ (53 g/l) containing HCl solution is added at the rate of 3.0 ml/min to the suspension in controlling the pH 1.8 by simultaneous addition of aqueous NaOH solution.

630 ml of aqueous solution of $TiCl_4$ (400 g/l) is added at the rate of 2.0 ml/min to the suspension in controlling the pH 1.8 by simultaneous addition of aqueous NaOH solution. Then 265 ml of aqueous solution of $SnCl_4$ (53 g/l) containing HCl solution is added at the rate of 3.0 ml/min to the suspension in controlling the pH 1.8 by simultaneous addition of aqueous NaOH solution. After adding the aqueous solution of $SnCl_4$ the aqueous solution of $TiCl_4$ (400 g/l) is added at the rate of 2.0 ml/min to the suspension in controlling the pH 1.6 by simultaneous addition of aqueous NaOH solution.

After reaching to end point of Red.

The pH value of the suspension is controlled pH 9.0 by adding aqueous NaOH solution. The suspension containing mica coated with metal hydroxide is filtrated and washed by deionized water. The filter cake is dried at 110° C. and the dried product is calcinated at 750° C.

Example 3

147 g of fine-mica powder of 1 to 15 μm (average particle diameter: 6.5 μm) are suspended in 2.1 liters of deionized water. The suspension is heated to 75° C. while stirring. The pH is adjusted to 9.5 by adding sodium hydroxide. 271 ml of aqueous solution of $SnCl_4$ (53 g/l) containing HCl solution is added at the rate of 3.5 ml/min to the suspension in controlling the pH 1.8 by simultaneous addition of aqueous NaOH solution. 250 ml of aqueous solution of $TiCl_4$ (400 g/l) is added at the rate of 2.5 ml/min to the suspension in controlling the pH 1.8 by simultaneous addition of aqueous NaOH solution. Then 271 ml of aqueous solution of $SnCl_4$ (53 g/l) containing HCl solution was added at the rate of 3.5 ml/min to the suspension in controlling the pH 1.8 by simultaneous addition of aqueous NaOH solution. After adding the aqueous solution of $SnCl_4$ the aqueous solution of $TiCl_4$ (400 g/l) is added at the rate of 5.5 ml/min to the suspension in controlling the pH 1.6 by simultaneous addition of aqueous NaOH solution.

After reaching to end point of Blue.

The pH value of the suspension is controlled pH 9.0 by adding aqueous NaOH solution. The suspension containing mica coated with metal hydroxide is filtrated and washed by deionized water. The filter cake is dried at 110° C. and the dried product is calcinated at 750° C.

Example 4

140 g of fine-mica powder of 1 to 15 μm (average particle diameter: 6.5 μm) are suspended in 2.0 liters of deionized water. The suspension is heated to 75° C. while stirring. The pH is adjusted to 9.5 by adding sodium hydroxide. 290 ml of aqueous solution of $SnCl_4$ (53 g/l) containing HCl solution is added at the rate of 3.5 ml/min to the suspension in controlling the pH 1.8 by simultaneous addition of aqueous NaOH solution.

250 ml of aqueous solution of $TiCl_4$ (400 g/l) is added at the rate of 5.0 ml/min to the suspension in controlling the pH 1.8 by simultaneous addition of aqueous NaOH solution. Then 270 ml of aqueous solution of $SnCl_4$ (53 g/l) containing HCl solution is added at the rate of 3.5 ml/min to the suspension in controlling the pH 1.8 by simultaneous addition of aqueous NaOH solution. After adding the aqueous solution of $SnCl_4$ the aqueous solution of $TiCl_4$ (400 g/l) is added at the rate of 5.5 ml/min to the suspension in controlling the pH 1.6 by simultaneous addition of aqueous NaOH solution.

After reaching to end point of Green.

Thereafter, 4.0 g of $MgCl_2 \cdot 6H_2O$ and 8 g of $CaCl_2 \cdot 2H_2O$ are added. Then, the pH value of the suspension is controlled pH 9.0 by adding aqueous NaOH solution. The suspension containing mica coated with metal hydroxide is filtrated and washed by deionized water. The filter cake is dried at 110° C. and the dried product is calcinated at 750° C.

Use Examples

Examples A1.1 to A1.4: Oil-in-Water Formulation

| Example Ingredient | INCI | BLANK % w/w | A1.1 % w/w | A1.2 % w/w | A1.3 % w/w | A1.4 % w/w |
|---|---|---|---|---|---|---|
| Phase A | | | | | | |
| Pigment according to Example 3 | TITANIUM DIOXIDE, MICA, TIN OXIDE | | a) 5.00 b) 3.00 | | | |
| Pigment according to Example 1 | TITANIUM DIOXIDE, MICA, TIN OXIDE | | | a) 5.00 b) 3.00 | | |
| Pigment according to Example 4 | TITANIUM DIOXIDE, MICA, TIN OXIDE | | | | a) 5.00 b) 3.00 | |
| Pigment according to Example 2 | TITANIUM DIOXIDE, MICA, TIN OXIDE | | | | | a) 5.00 b) 3.00 |
| Montanov 202 | ARACHIDYL ALCOHOL, BEHENYL ALCOHOL, ARACHIDYL GLUCOSIDE | 3.50 | 3.50 | 3.50 | 3.50 | 3.50 |
| Montanov 14 | MYRISTYL ALCOHOL, MYRISTYL GLUCOSIDE | 1.50 | 1.50 | 1.50 | 1.50 | 1.50 |
| Tegosoft TN | C12-15 ALKYL BENZOATE | 8.00 | 8.00 | 8.00 | 8.00 | 8.00 |
| Massocare HD | ISOHEXADECANE | 4.00 | 4.00 | 4.00 | 4.00 | 4.00 |
| Miglyol 812 | CAPRYLIC/ CAPRIC TRIGLYCERIDE | 10.00 | 10.00 | 10.00 | 10.00 | 10.00 |
| Phase B | | | | | | |
| Glycerin 85% | GLYCERIN | 4.00 | 4.00 | 4.00 | 4.00 | 4.00 |
| Keltrol CG-RD | XANTHAN GUM | 0.80 | 0.80 | 0.80 | 0.80 | 0.80 |
| Wasser | AQUA | 67.2 | 62.20 | 62.20 | 62.20 | 62.20 |
| Phase C | | | | | | |
| Euxyl PE 9010 | PHENOXYETHANOL, ETHYLHEXYLGLYCERIN | 1.00 | 1.00 | 1.00 | 1.00 | 1.00 |
| | sum | 100.00 | 100.00 | 100.00 | 100.00 | 100.00 |

Procedure:

Heat up phase A up to 75-80° C. Disperse Pigment according to Examples 1 to 4 in phase A while holding the temperature at 75-80° C. Disperse Keltrol CG-RD while stirring in phase B and heat up to 75-80° C. Add phase A to phase B and homogenize with Ultra Turrax T-25 for 2.5 minutes at 8000 rpm. Cool down while stirring to room temperature and add phase C while stirring.

Example A2: Gel Formulation

| Ingredient | INCI | % w/w |
|---|---|---|
| Phase A | | |
| RonaCare ® AP | BIS-ETHYLHEXYL HYDROXYDIMETHOXY BENZYLMALONATE | 2.00 |
| Paraffin liquid | PARAFFINUM LIQUIDUM | 2.00 |
| Crodamol DA | DIISOPROPYL ADIPATE | 7.00 |
| Xiameter ® PMX-0345 | CYCLOPENTASILOXANE, CYCLOHEXASILOXANE | 5.00 |
| Phase B | | |
| Sepiplus 400 | POLYSORBATE 20, POLYACRYLATE 13, POLYISOBUTENE | 2.00 |
| Phase C | | |
| Pigment according to Example 4 | CI 77891, MICA, TIN OXIDE | 4.00 |
| RonaFlair ® LDP White | SODIUM POTASSIUM ALUMINUM SILICATE, CI 77891, SILICA | 2.00 |
| RonaCare ® Salicylic Acid | SALICYLIC ACID | 1.00 |
| Glycerol 85% | GLYCERIN, AQUA | 3.00 |
| RonaCare ® Ectoin | ECTOIN | 0.50 |
| Titriplex ® III | DISODIUM EDTA | 0.10 |
| Euxyl PE 9010 | PHENOXYETHANOL, ETHYLHEXYL GLYCERIN | 1.00 |
| Water, demineralized | AQUA | ad 100 |
| Phase D | | |
| Fragrance | PARFUM | q.s. |
| sum | | 100.00 |

Procedure:

Dissolve ingredients of phase A until homogenous.

Add B under stirring in the premixed phase C.

Add slowly phase A to phase B/C while stirring. Homogenize. Finally add phase D.

Example A3: Gel Formulation

| Ingredient | INCI | % w/w |
|---|---|---|
| Phase A | | |
| Colorona ® SynBronze | SYNTHETIC FLUORPHLOGOPITE, CI 77491 | 2.00 |
| Pigment according to Example 1 | CI 77891, MICA, TIN OXIDE | 1.00 |
| Carbopol Ultrez 21 | ACRYLATES/C10-30 ALKYL ACRYLATE CROSSPOLYMER | 0.60 |
| Citric Acid Monohydrate | CITRIC ACID | 0.00 |
| Water, demineralized | AQUA | ad 100 |
| Phase B | | |
| 1.2-Propanediol | PROPYLENE GLYCOL | 3.00 |
| RonaCare ® Allantoin | ALLANTOIN | 0.20 |
| Water, demineralized | AQUA | 26.46 |
| Phase C | | |
| Paraffin liquid | PARAFFINUM LIQUIDUM | 10.00 |
| Cetiol V | DECYL OLEATE | 6.00 |
| Hostaphat KL 340 D | TRILAURETH-4 PHOSPHATE | 3.00 |
| Cetyl Alcohol | CETYL ALCOHOL | 2.00 |
| Preservatives (q.s.) | | 0.00 |
| Phase D | | |
| Triethanolamine | TRIETHANOLAMINE | 0.35 |
| Water, demineralized | AQUA | 3.50 |
| Phase E | | |
| German 115 | IMIDAZOLIDINYL UREA | 0.15 |
| Water, demineralized | AQUA | 1.50 |
| Phase F | | |
| Fragrance | PARFUM | q.s. |

Procedure:

Disperse the pearlescent pigment in the given water quantity of phase A. Add some drops of citric acid solution to lower the viscosity and add the Carbopol while stirring. Mix with high agitation until thoroughly dispersed. Dissolve phase B and add phase B slowly to phase A while stirring. Heat phase A/B and phase C separately to 80° C. Add phase C to phase A/B, homogenize, neutralize with phase D, homogenize again and cool down while stirring. Add phase E and phase F at 40° C. Cool down to room temperature while stirring. The pH is between 5.5 and 6.0 at room temperature. Fill the bulk into packages of choice.

Example A4: Gel

| Ingredient | INCI | % w/w |
|---|---|---|
| Phase A | | |
| RonaCare ® AP | BIS-ETHYLHEXYL HYDROXYDIMETHOXY BENZYLMALONATE | 0.50 |
| Miglyol 812 N | CAPRYLIC/CAPRIC TRIGLYCERIDE | 3.00 |
| Cetiol CC | DICAPRYLYL CARBONATE | 2.50 |
| Sepinov P88 | SODIUM ACRYLATE, ACRYLOYL DIMETHYLTAURATE, DIMETHYLACRYLAMIDE CROSSPOLYMER | 2.00 |

-continued

| Ingredient | INCI | % w/w |
|---|---|---|
| Xiameter® PMX-0345 | CYCLOPENTASILOXANE, CYCLOHEXASILOXANE | 2.00 |
| Xiameter® PMX-200 (100 cs) | DIMETHICONE | 1.00 |
| Phase B | | |
| RonaFlair® White Sapphire | SYNTHETIC SAPPHIRE | 3.00 |
| Pigment according to Example 1 | CI 77891, MICA, TIN OXIDE | 2.00 |
| Eusolex® UV-Pearls® OB-S | AQUA, OCTOCRYLENE, SORBITOL, BUTYL METHOXYDIBENZOYLMETHANE, SILICA, PVP, CHLORPHENESIN, PHENOXYETHANOL, DISODIUM EDTA | 15.00 |
| 1.3-Butanediol | BUTYLENE GLYCOL | 3.00 |
| Water, demineralized | AQUA | ad 100 |
| Phase C | | |
| RonaCare® Cyclopeptide-5 | AQUA, ALCOHOL, LECITHIN, ECTOIN, CYCLOTETRAPEPTIDE-24 AMINOCYCLOHEXANE CARBOXYLATE | 2.00 |
| Euxyl PE 9010 | PHENOXYETHANOL, ETHYLHEXYL GLYCERIN | 1.00 |
| Fragrance | PARFUM | q.s. |

Procedure:

Add phase B slowly with vigorous stirring to phase A. Homogenize. Afterwards add phase C.

Example A5: Oil-in-Water Emulsion

| Ingredient | INCI | % w/w |
|---|---|---|
| Phase A | | |
| Water, demineralized | AQUA (WATER) | ad 100 |
| Glycerol 85% | GLYCERIN, AQUA (WATER) | 6.00 |
| Pigment according to Example 2 | CI 77891 (TITANIUM DIOXIDE), MICA, TIN OXIDE | 1.50 |
| Pigment according to Example 3 | CI 77891 (TITANIUM DIOXIDE), MICA, TIN OXIDE | 1.50 |
| RonaCare® Ectoin | ECTOIN | 1.00 |
| Keltrol CG-SFT | XANTHAN GUM | 0.15 |
| Triethanolamine | TRIETHANOLAMINE | 0.11 |
| Phase B | | |
| Titanium-(IV)-oxid | TITANIUM DIOXIDE | 6.00 |
| Unipure Yellow LC 182 | CI 77492 (IRON OXIDES) | 0.50 |
| Unipure Red LC 381 | CI 77491 (IRON OXIDES) | 0.10 |
| Unipure Brown LC 889 | CI 77491 (IRON OXIDES), CI 77499 (IRON OXIDES) | 0.05 |
| Unipure Blue LC 686 | CI 77007 (ULTRAMARINE BLUE) | 0.03 |
| Phase C | | |
| Eusolex® OCR | OCTOCRYLENE | 8.00 |
| Eusolex® 9020 | BUTYL METHOXYDIBENZOYLMETHANE | 1.50 |
| Miglyol 812 N | CAPRYLIC/CAPRIC TRIGLYCERIDE | 7.00 |
| Eutanol G | OCTYLDODECANOL | 4.00 |
| Montanov 202 | ARACHIDYL ALCOHOL, BEHENYL ALCOHOL, ARACHIDYLGLUCOSIDE | 4.00 |
| Avocado Oil | PERSEA GRATISSIMA (AVOCADO OIL) | 2.00 |
| Hydrolite-5 | PENTYLENE GLYCOL | 1.20 |
| RonaCare® AP | BIS-ETHYLHEXYL HYDROXYDIMETHOXY BENZYLMALONATE | 1.00 |
| Bentone Gel GTCC V | STEARALKONIUM HECTORITE, PROPYLENE CARBONATE, CAPRYLIC/CAPRIC TRIGLYCERIDE | 1.00 |
| Oxynex® K liquid | PEG-8, TOCOPHEROL, ASCORBYL PALMITATE, ASCORBIC ACID, CITRIC ACID | 0.03 |
| Phase D | | |
| Simulgel EG | SODIUM ACRYLATE/SODIUM ACRYLOYLDIMETHYLTAURATE COPOLYMER, ISOHEXADECANE, POLYSORBATE 80 | 0.60 |
| Phase E | | |
| Fragrance | | q.s. |
| Preservative | | q.s. |

Procedure:

Disperse Keltrol slowly in the remainder of phase A while stirring. Add phase B and homogenize with an Ultra-Turrax T25 at a speed of approx. 17000 rpm for 5 min. Check that phase A/B is free of agglomerates. Heat phase A/B and phase C separately to 85° C. Add phase C to A/B while stirring and homogenize with an Ultra-Turrax T25 (speed slow-middle; approx. 9500 rpm) for about 2 min. At 55-60° C. add phase D while stirring. Cool down to room temperature while stirring and add phase E. Adjust pH to 6.7-6.9.

Example A6: Oil-in-Water Emulsion

| Ingredient | INCI | % w/w |
|---|---|---|
| Phase A | | |
| Pigment according to Example 3 | CI 77891, MICA, TIN OXIDE | 1.00 |
| Pigment according to Example 2 | CI 77891, MICA, TIN OXIDE | 1.00 |
| RonaFlair® White Sapphire | SYNTHETIC SAPPHIRE | 1.00 |
| Water, demineralized | AQUA | ad 100 |
| Glycerol 85% | GLYCERIN, AQUA | 4.00 |
| Hydrolite-5 | PENTYLENE GLYCOL | 2.00 |
| RonaCare® Biotin Plus | UREA, SODIUM PHOSPHATE, BIOTIN, CITRIC ACID | 1.00 |
| D-Panthenol | PANTHENOL | 0.50 |
| RonaCare® Ectoin | ECTOIN | 0.30 |
| Methyl-4-hydroxybenzoate | METHYLPARABEN | 0.15 |
| Phase B | | |
| Montanov 68 | CETEARYL ALCOHOL, CETEARYL GLUCOSIDE | 4.00 |
| Dow Corning 9040 Silicone Elastomer Blend | CYCLOMETHICONE, DIMETHICONE CROSSPOLYMER | 2.50 |

-continued

| Ingredient | INCI | % w/w |
|---|---|---|
| Tegosoft DEC | DIETHYLHEXYL CARBONATE | 2.00 |
| Cosmacol ELI | C12-13 ALKYL LACTATE | 2.00 |
| Arlamol HD | ISOHEXADECANE | 2.00 |
| Xiameter ® PMX-0345 | CYCLOPENTASILOXANE, CYCLOHEXASILOXANE | 2.00 |
| Span 60 | SORBITAN STEARATE | 1.50 |
| Lanette 0 | CETEARYL ALCOHOL | 1.00 |
| Olive Oil, bio | OLEA EUROPAEA | 0.50 |
| RonaCare ® AP | BIS-ETHYLH EXYL HYDROXYDIMETHOXY BENZYLMALONATE | 0.50 |
| Propyl-4-hydroxybenzoate | PROPYLPARABEN | 0.05 |
| Phase C | | |
| Rhodicare S | XANTHAN GUM | 0.25 |
| Phase D | | |
| Fragrance | PARFUM | q.s. |

Procedure:

Heat phase A and B separately to 75° C. Add phase C slowly to phase A while stirring until a homogeneous mixture is obtained. At 75° C. add phase B to phase A/C and homogenize for 1 min. (Ultra Turrax T25 at 8000 rpm). Cool down to 35° C. and add perfume. Cool down to room temperature while stirring. Adjust pH value between 5.0-5.5.

Example A7: Oil-in-Water Emulsion

| Ingredient | INCI | % w/w |
|---|---|---|
| Phase A | | |
| Water, demineralized | AQUA | ad 100 |
| Chelating Agent | | 0.10 |
| 1,2-Propanediol | PROPYLENE GLYCOL | 4.00 |
| Lecigel | SODIUM ACRYLATES COPOLYMER, LECITHIN | 1.00 |
| RonaCare ® Ectoin | ECTOIN | 0.50 |
| Phase B | | |
| Sensanov ™ WR | C20-22 ALKYL PHOSPHATE, C20-22 ALCOHOLS | 3.50 |
| Tego ® Alkanol 1618 | CETEARYL ALCOHOL | 2.00 |
| RonaFlair ® SynMica M | SYNTHETIC FLUORPHLOGOPITE | 2.00 |
| Pigment according to Example 3 | CI 77891, MICA, TIN OXIDE | 1.00 |
| RonaCare ® AP | BIS-ETHYLHEXYL HYDROXYDIMETHOXY BENZYLMALONATE | 1.00 |
| Tegosoft ® DC | DECYL COCOATE | 1.50 |
| RonaCare ® Pristine Bright ™ | METHOXYPHENYL T-BUTYLPHENYL PROPANEDIOL | 2.00 |
| Tegosoft CT | CAPRYLIC/CAPRIC TRIGLYCERIDE | 4.00 |
| IPM | ISO PROPYL MYRISTATE | 2.00 |
| Phase C | | |
| TEA | TRIETHANOLAMINE | 0.18 |
| Phase D | | |
| Euxyl PE 9010 | PHENOXYETHANOL, ETHYLHEXYL GLYCERIN | 0.80 |
| Xiameter ® PMX-0245 | CYCLOPENTASILOXANE | 1.00 |
| Perfume | | q.s. |

Procedure:
1. Disperse Lecigel in water and add all the ingredients of A.
2. Heat A and B at 80° C. and mix well.
3. Add C while mixing and homogenize well.
4. Add Phase D at 35° C.

Example A8: Water-in-Silicone Emulsion

| Ingredient | INCI | % w/w |
|---|---|---|
| Phase A | | |
| Water, demineralized | AQUA | 44.00 |
| RonaCare ® Sodium Chloride | SODIUM CHLORIDE | 1.00 |
| 1,3-Butanediol | BUTYLENE GLYCOL | 5.00 |
| Eumulgin SG | SODIUM STEAROYL GLUTAMATE | 0.50 |
| Ethanol 96% | ALCOHOL | 4.00 |
| Caffeine | CAFFEINE | 0.50 |
| MinaCare Freshin | METHYL DIISOPROPYL PROPIONAMIDE | 0.40 |
| RonaCare ® Cyclopeptide-5 | AQUA, ALCOHOL, LECITHIN, ECTOIN, CYCLOTETRAPEPTIDE-24 AMINOCYCLOHEXANE CARBOXYLATE | 3.00 |
| Microcare PM2 | PHENOXYETHANOL, ETHYLPARABEN, METHYLPARABEN | 1.00 |
| Phase B | | |
| Xiameter ® PMX-200 Silicone Fluid (10 cs) | DIMETHICONE | 6.00 |
| Xiameter ® PMX-0345 | CYCLOPENTASILOXANE, CYCLOHEXASILOXANE | 8.00 |
| Bentone gel VS-5 PC V | CYCLOMETHICONE, QUATERNIUM-18 HECTORITE, PROPYLENE CARBONATE | 2.50 |
| Eusolex ® 2292 | ETHYLHEXYL METHOXYCINNAMATE | 5.00 |
| Dow Corning 556 | PHENYL TRIMETHICONE | 5.00 |
| Dow Corning ES 5612 | PEG-10 DIMETHICONE | 4.00 |
| RonaCare ® Poppy SE | CAPRYLIC/CAPRIC TRIGLYCERIDE, PAPAVER RHOEAS EXTRACT, TOCOPHEROL | 1.00 |
| Oxynex ® ST Liquid | DIETHYLHEXYL SYRINGYLIDENE MALONATE, CAPRYLIC/CAPRIC TRIGLYCERIDE | 0.10 |
| Phase C | | |
| Silkflo 366 NF | HYDROGENATED POLYDECENE | 3.00 |
| Abil EM 97 | BIS-PEG/PPG-14/14 DIMETHICONE, CYCLOPENTASILOXANE | 3.00 |
| Colorona ® Oriental Beige | MICA, CI 77891, CI 77491 | 0.10 |
| RonaFlair ® Boroneige ® SF-3 | BORON NITRIDE | 1.00 |
| Pigment according to Example 1 | CI 77891, MICA, TIN OXIDE | 1.50 |
| Phase D | | |
| Fragrance (q.s.) | PARFUM | 0.40 |

Procedure:

Prepare phase A (premix Minacare Freshin and Coffein in alcohol before adding to remaining ingredients). Prepare phase B then add C to B under stirring. Mix A with C+B. Add perfume.

Measurement of the HEV, VIS and IR-A Absorption of Examples A1.1 to A1.4

In order to obtain information regarding the protection potential of different formulations against IR-A or HEV light the transmission and reflection of the formulations are measured at different wavelengths. The formulations A1.1. to A1.4 containing interference pigments according to Examples 1 to 4 are put in a 100 μm cuvette (disintegration cuvette) and then measured in the UV-VIS-NIR spectrometer Lambda 900. The device parameters are summarized in the following table.

TABLE

| Device settings for the Lambda 900 | |
|---|---|
| Wavelength/nm | 250-1450 |
| Baseline | Glycerin Transmission/Glycerin Reflection |
| Spectral gap width/nm | 4 |
| Integration time/s | 0.2 |
| Increment/nm | 0.5 |
| Layer thickness of the sample | 0.1 mm |
| Temperature | Room temperature |
| Common Beam Depolarizer | ON |
| Method | Measuring transmission and reflection |
| Focusing | T-focused/R-focused with lens |

In the following are given the results of the of the HEV, VIS and IR-A absorption with the interference pigments according to the present invention.

1. Protection Against HEV Light in Oil-in-Water Formulation

The area under the measured transmission curve between 400-500 nm for HEV light is calculated and displayed as a bale plot. The lower the transmission the higher the protection of the formulation. The results are summarized in FIG. 1a and FIG. 1b.

Surprisingly, 5% of interference pigments according to Examples 1 to 4 show a reduction in the transmission of HEV light up to 24% and enhance therefore the protection against it. The best performance is measured with the interference pigment according to Example 3. The results show that, increasing the pigment concentration from 3 to 5% increase the protection against HEV light up to 10%

2. Protection Against VIS Light in Oil-in-Water Formulation

The area under the measured transmission curve between 400-800 nm for VIS light is calculated and displayed as a bale plot. The lower the transmission the higher the protection of the formulation.

The results are summarized in FIG. 2a and FIG. 2b.

5% interference pigments show a reduction in the transmission of VIS light up to 21% and enhance therefore the protection against it. The best performance is measured with the interference pigment according to Example 1 followed by pigment of Example 4, followed by pigment of Example 3 and followed by pigment of Example 4.

The results show that, increasing the pigment concentration from 3 to 5% increase the protection against VIS light up to 10%.

3. Protection Against IR-A Light

The area under the measured transmission curve between 800-1450 nm for IR-A light is calculated and displayed as a bale plot. The lower the transmission the higher the protection of the formulation. The results are summarized in FIG. 3a and FIG. 3b.

5% interference pigments show a reduction in the transmission of IR-A light up to 26% and enhance therefore the protection against it. The best performance is measured with the pigment according to Example 3 followed by pigment according to Example 2, followed by pigment according to Example 1 and followed by pigment according to Example 4. The results show that, increasing the pigment concentration from 3 to 5% increase the protection against IR-A light up to 10%.

BRIEF DESCRIPTION OF THE DRAWINGS

FIG. 1a and FIG. 1b show the results of tests for protection against HEV light in oil-in-water formulation according to invention.

FIG. 2a and FIG. 2b show the results of tests for protection against VIS light in oil-in-water formulation according to invention.

FIG. 3a and FIG. 3b show the results of tests for protection against IR-A light for pigments according to the invention.

The invention claimed is:

1. An interference pigment based on a platelet shaped substrate with a particle diameter in the range 1-100 μm characterized in that the substrate is coated on the surface with at least four layers (A) to (D),
(A) is a refractive index layer which consist of $SnO_2$
(B) is a refractive index layer which consist of undoped $TiO_2$
(C) is a refractive index layer which consist of $SnO_2$
(D) is a refractive index layer which consist of undoped $TiO_2$
and optionally
(E) an outer protective layer.

2. The interference pigment according to claim 1, characterised in that the platelet-shaped substrate is selected from natural or synthetic mica, coated or uncoated glass flakes, $Al_2O_3$ flakes, $SiO_2$ flakes, $Fe_2O_3$ flakes, perlite flakes or $TiO_2$ flakes, passivated metal flakes and flake-form materials coated with metal oxides.

3. The interference pigment according to claim 2, characterised in that the flake-form substrate is selected from mica flakes, coated or uncoated glass flakes or $Al_2O_3$ flakes.

4. The interference pigment according to claim 2, characterized in that the glass flake is coated with a $SiO_2$ layer (layer (A0)).

5. The interference pigment according to claim 1, characterised in that the pigment has the following structure:

Synthetic mica+$SnO_2$+$TiO_2$+$SnO_2$+$TiO_2$

Natural mica+$SnO_2$+$TiO_2$+$SnO_2$+$TiO_2$ $Al_2O_3$ flakes+$SnO_2$+$TiO_2$+$SnO_2$+$TiO_2$ $SiO_2$ flakes+$SnO_2$+$TiO_2$+$SnO_2$+$TiO_2$ Glass flakes+$SiO_2$+$SnO_2$+$TiO_2$+$SnO_2$+$TiO_2$, or Glass flakes+$SnO_2$+$TiO_2$+$SnO_2$+$TiO_2$.

6. The interference pigment according to claim 4, characterised in that the thickness of all layers (A0)-(D) or (A)-(D) on the substrate is ≤300 nm.

7. The interference pigment according to claim 1, wherein the refractive index of the refractive index layer is greater than 1.8.

8. A formulation containing one or more interference pigments according to claim 1.

9. The formulation according to claim 8 characterized in that the formulation is a cosmetic formulation.

10. The formulation according to claim 9 characterized in that the cosmetic formulation is an oil-in-water emulsion, a water-in-oil emulsion, a water-in-silicone emulsion or a gel.

11. The formulation according to claim 8 characterized in that the formulation additionally contains at least one constituent selected from the group of absorbents, astringents, antimicrobial substances, antioxidants, antiperspirants, antifoaming agents, antidandruff active compounds, antistatics, binders, biological additives, bleaches, chelating agents, deodorisers, emollients, emulsifiers, emulsion stabilisers, dyes, humectants, film formers, fillers, fragrances, flavours, insect repellents, preservatives, anticorrosion agents, cosmetic oils, solvents, oxidants, vegetable constituents, buffer substances, reducing agents, surfactants, propellant gases, opacifiers, UV filters, UV absorbers, denaturing agents, viscosity regulators, perfume and vitamins.

12. The formulation according to claim 8 characterized in that the formulation contains additionally one or more organic or inorganic UV filters.

13. A process for preparing the interference pigment of claim 1, wherein the metal oxides are applied to the flake-form substrate by wet-chemical methods by hydrolytic decomposition of metal salts in aqueous medium.

14. A method for pigmenting a composition comprising incorporating the interference pigment according to claim 1 in a composition for paints, coatings, industrial coatings, coil coating, automobile paints, automotive refinish paints, powder coatings, printing inks, security printing inks, plastics, ceramic materials, cosmetic formulations, glasses, paper, toners for electrophotographic printing processes, seeds, greenhouse sheeting or tarpaulins, absorbers in the laser marking of paper and plastics, cosmetic formulations, for preparation of pigment pastes with water, organic and/or aqueous solvents, preparation of pigment preparations or dry preparations, mass colouring of foods, colouring of coatings of food products or pharmaceutical products or a protecting agent against IR-A, VIS and HEV light.

\* \* \* \* \*